United States Patent [19]

Logothetis et al.

[11] Patent Number: 4,487,680
[45] Date of Patent: Dec. 11, 1984

[54] PLANAR ZRO₂ OXYGEN PUMPING SENSOR

[75] Inventors: Eleftherios M. Logothetis; William C. Vassell, both of Birmingham, Mich.

[73] Assignee: Ford Motor Company, Dearborn, Mich.

[21] Appl. No.: 505,036

[22] Filed: Apr. 18, 1983

[51] Int. Cl.³ .................................................. G01N 27/46
[52] U.S. Cl. .................................... 204/426; 204/425; 204/427; 204/412
[58] Field of Search ................ 204/1 S, 412, 421–429

[56] References Cited

U.S. PATENT DOCUMENTS

| | | | |
|---|---|---|---|
| 3,791,937 | 2/1974 | Besson et al. | 204/1 S |
| 4,101,403 | 7/1978 | Kita et al. | 204/429 |
| 4,207,159 | 6/1980 | Kimura et al. | 204/425 |
| 4,264,425 | 4/1981 | Kimura et al. | 204/429 |
| 4,298,573 | 11/1981 | Fujishiro | 204/425 |
| 4,300,991 | 11/1981 | Chiba et al. | 204/426 |
| 4,302,312 | 11/1981 | Ishitani et al. | 204/426 |
| 4,306,957 | 12/1981 | Ishitani et al. | 204/426 |
| 4,377,460 | 3/1983 | Hirayama et al. | 204/1 S |

Primary Examiner—T. Tung
Attorney, Agent, or Firm—Peter Abolins; Robert D. Sanborn

[57] ABSTRACT

A planar oxygen pumping device (10) has a first and second oxygen ion conductive solid electrolyte material layer (12, 18). A first electrode (16) is between, and in contact with, the first electrolyte material layers and the second electrolyte material layer. A second electrode (14) is on the first electrolyte material layer. A third electrode (20) is on the second electrolyte material layer. At least one of the first and second electrolyte layers has a porosity sufficient to establish at the first electrode (16) an oxygen concentration dependent upon the ambient atmosphere.

1 Claim, 5 Drawing Figures

PLANAR ZRO₂ OXYGEN PUMPING SENSOR

TECHNICAL FIELD

This invention relates to an apparatus for measuring the concentration of oxygen. The apparatus includes an oxygen ion conductive solid electrolyte material layer.

BACKGROUND ART

In recent years, there has been an increased demand for high temperature oxygen sensors, mainly for the monitoring and control of combustion processes, such as the combustion of hydrocarbons in an internal combustion engine. One device of this type widely used for automative engine control is an electrochemical oxygen concentration cell, usually made of zirconia ($ZrO_2$). In the most common configuration of this device, the $ZrO_2$ electrolyte is in the form of a thimble with one side exposed to the combustion environment and the other exposed to air as a reference atmosphere. This device provides an EMF output which is proportional to the logarithm of the oxygen partial pressure in the combustion environment.

Despite its low sensitivity, this device is widely used on automobiles to control and maintain the air-to-fuel mixture in the engine cylinder at the stoichiometric value. A stoichiometric mixture contains just enough oxygen to burn the fuel completely to carbon dioxide and water. The satisfactory operation of this device arises from the fact that the oxygen partial pressure in the product of combustion (exhaust gas) changes by many orders of magnitude (for example, twenty) as the air-to-fuel mixture is varied through the stoichiometric value.

On the other hand, for the purpose of reducing fuel consumption, it is generally desirable to operate internal combustion engines with "lean" air-to-fuel mixtures, which contain excess air. For these lean mixtures, the oxygen partial pressure after combustion exhibits only a small and gradual change with change in the air-to-fuel mixture. These small changes cannot be easily measured with the above-mentioned device. One approach for obtaining high sensitivity devices for use in lean air-to-fuel operation is to employ a so-called oxygen-pumping scheme. Such oxygen-pumping is based on the fact that if a current is passed through an oxygen-conducting electrolyte (e.g. zirconia), oxygen is transferred (pumped) from one side of the electrolyte to the other. Several oxygen sensors based on this principle have been described in the prior art. Examples are those described in U.S. Pat. Nos. 3,923,624 to Beckman et al; 3,654,112 to Beckman et al; 3,907,657 to Heijne et al; and 3,698,384 to Jayes.

Recently a series of U.S. patents to Hetrick and Hetrick et al. (U.S. Pat. Nos. 4,272,320; 4,272,330; 4,272,331) describe an oxygen-pumping device that has improved characteristics over previously described devices, e.g., higher speed of response, lower sensitivity to temperature variations and independence from ambient total pressure changes. These features make this device particularly useful for automotive engine use. This device has two pieces of dense zirconia sealed together to form a cavity that communicates with the outside volume through one or more apertures. Electrodes are deposited on the inside and outside walls of each of the two sections of the device, thus forming an oxygen pumping cell and a sensing cell. The fabrication of this device involves several steps, one step being the sealing of the device with glass frit. Having to seal pieces of zirconia in the fabrication of such a prior art device presents problems with respect to durability and cost. It would be desirable to avoid the need for sealing an enclosed volume. It would also be desirable to use fewer electrodes. In addition to simplified fabrication, it would be desirable to increase reproducibility and reliability and have operation occur at a lower temperature. These are some of the problems this invention overcomes.

DISCLOSURE OF THE INVENTION

An oxygen pumping device responsive to the oxygen partial pressure in a gas includes first and second oxygen ion conductive solid electrolyte material layers and first, second and third electrodes. The first oxygen ion conductive solid electrolyte material layer has a first porosity. The second oxygen ion conductive solid electrolyte material layer has a second porosity, which can be different from the first porosity, and is in contact with the first electrolyte material layer. The first electrode is between, and in contact with, the first electrolyte material layer and the second electrolyte material layer. The second electrode is on the first electrolyte material layer. The third electrode is on the second electrolyte material layer.

As a result, only three electrodes are required to form a oxygen pump and an oxygen sensor. The oxygen pumping device eliminates the need for fabricating the enclosed volume of the prior art. Since the enclosure can be eliminated, the present devices can be easily fabricated by established planar technologies for the preparation of the various layers which eliminates the need for sealing together the various parts of the device of the prior art. In addition to the simplification in fabrication and lower cost, the application of planar technology will result in an increased reproducibility, accuracy and reliability of the device. Furthermore, a lower operating temperature is possible because of the decreased impedance in the direction of the current flow resulting from the reduction in thickness of the two electrolyte layers.

When one electrolyte layer with its two adjacent electrodes is used as an oxygen pump, and the other electrolyte layer with its two adjacent electrodes is used as an oxygen sensing electrochemical cell, if the pump current is chosen so that the sensing cell output is constant and equal to a prescribed value, the value of the pump current is proportional to the oxygen partial pressure of the environment in which the device is placed.

BEST MODE FOR CARRYING OUT THE INVENTION

Figure 1:
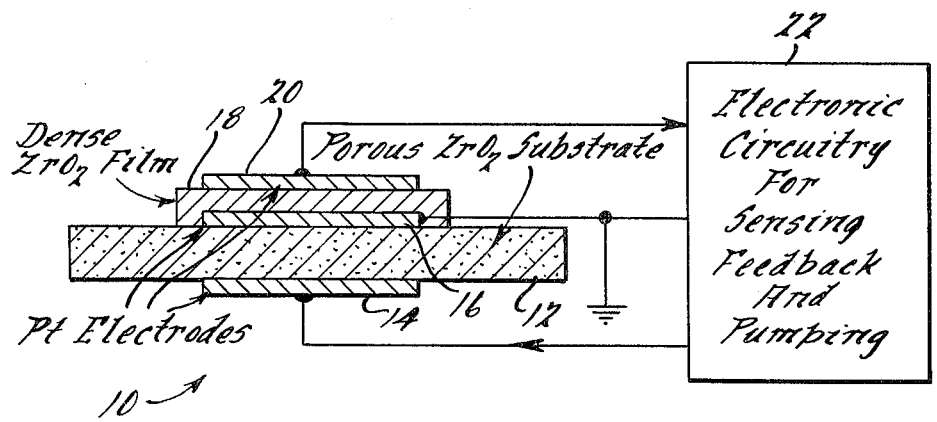
FIG. 1 is a cross section view of an oxygen pumping device in accordance with a first embodiment of this invention wherein a porous electrolyte material is used as a substrate.

Referring to FIG. 1, an oxygen measuring device 10 includes a porous oxygen-ion-conducting solid electrolyte substrate layer 12. The term porous material is used herein to mean that the material possess a nontrivial permeability to gases. Advantageously, the porosity provides sufficient permeability to gases so that the oxygen concentration within at least a portion of layer 12 is dependent upon the oxygen concentration in the ambient atmosphere. The substrate 12 has sufficient mechanical strength to act as the support for the entire device 10. An electrode 14 is formed on one surface of substrate 12 and an electrode 16 is formed on the opposing surface of substrate 12. A layer of an oxygen-ion-conducting electrolyte 18, advantageously, but not necessarily, of the same chemical composition as substrate layer 12, is formed over electrode 16 and extends onto the adjacent surface of substrate layer 12. Solid electrolyte layer 18 is more dense, substantially impermeable to gases and generally thinner than substrate layer 12. An electrode 20 is formed on the surface of solid electrolyte layer 18 on the opposite side of electrode 16.

Electrodes 14, 16 and 20 are connected to an electric circuit 22 which measures signal output and controls the operation of device 10. Oxygen measuring device 10 has two electrochemical cells. The first cell includes electrode 14, electrolyte substrate layer 12 and electrode 16 and is used as an oxygen pumping cell by passing constant current, I, supplied by electric circuit 22. The second electrochemical cell includes electrode 16, electrolyte layer 18 and electrode 20, and is used as a sensor to sense the oxygen pressure difference existing between electrodes 16 and 20.

In operation, the device is completely immersed in the atmosphere whose oxygen content is to be measured. Device 10 is maintained at some high temperature, preferably by a heater which is an integral part of the oxygen sensor. When a DC current I is passed through the pumping cell in the direction indicated in FIG. 1, oxygen ions move through electrolyte layer 12 in the direction from electrode 16 to electrode 14. The continuous flow of oxygen ions ($O^{2-}$) is maintained by the following electrochemical reactions at electrodes 16 and 14:

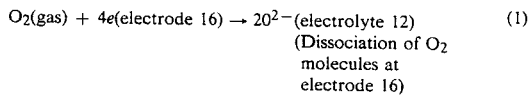

$$O_2(gas) + 4e(\text{electrode } 16) \rightarrow 2O^{2-}(\text{electrolyte } 12) \quad (1)$$
(Dissociation of $O_2$ molecules at electrode 16)

and

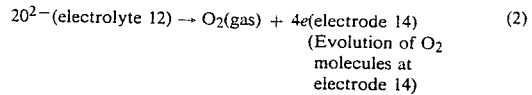

$$2O^{2-}(\text{electrolyte } 12) \rightarrow O_2(gas) + 4e(\text{electrode } 14) \quad (2)$$
(Evolution of $O_2$ molecules at electrode 14)

The net effect of the current is to transfer $O_2$ molecules from the neighborhood of electrode 16 to the neighborhood of electrode 14. The depletion of $O_2$ molecules at electrode 16 will cause diffusional flow of $O_2$ molecules from the ambient through the pores of the porous electrolyte layer 12 to the electrode 16. At steady state conditions, a flux, $F_D$, of gaseous $O_2$ will be equal to the flux of $O_2$ delivered at electrode 14 by current I:

$$F_D = \frac{I}{4e} \quad (3)$$

Under these conditions, the oxygen partial pressure, $P_i$, in electrolyte layer 12 at electrode 16 will be lower than the ambient oxygen partial pressure $P_x$. The value $P_i$ will depend on the magnitude of the current, and the porosity and geometery of electroylte layer 12. Under conditions of molecular flow the flux $F_D$ is given by:

$$F_D = \sigma_L(P_x - P_i) \quad (4)$$

where $\sigma_L$ = constant. Hence, $$I = 4e\sigma_L(P_x - P_i) \quad (5)$$

wherein:
- $\sigma_L$ is a constant which is a function of porosity, temperate and the diffusion constant of oxygen;
- $P_x$ is the ambient oxygen partial pressure to be measured;
- $P_i$ is the oxygen partial pressure in a portion of the electrolyte layer.

The presence of a lower oxygen partial pressure $P_i$ at electrode 16 will cause an electromotive force $V_s$ to develop across the sensing cell consisting of electrode 16, dense electrolyte layer 18 and electrode 20 with a value given by:

$$V_s = \frac{RT}{4Fe} \ln \frac{P_x}{P_i} \quad (6)$$

wherein:
- R is the ideal gas constant
- T is the temperature
- e is the electron charge From equations (5) and (6) one obtains:

$$I = 4eP_x \sigma_L \left[ 1 - \exp\left( -\frac{4FV_s}{RT} \right) \right] \quad (7)$$

Figure 2:
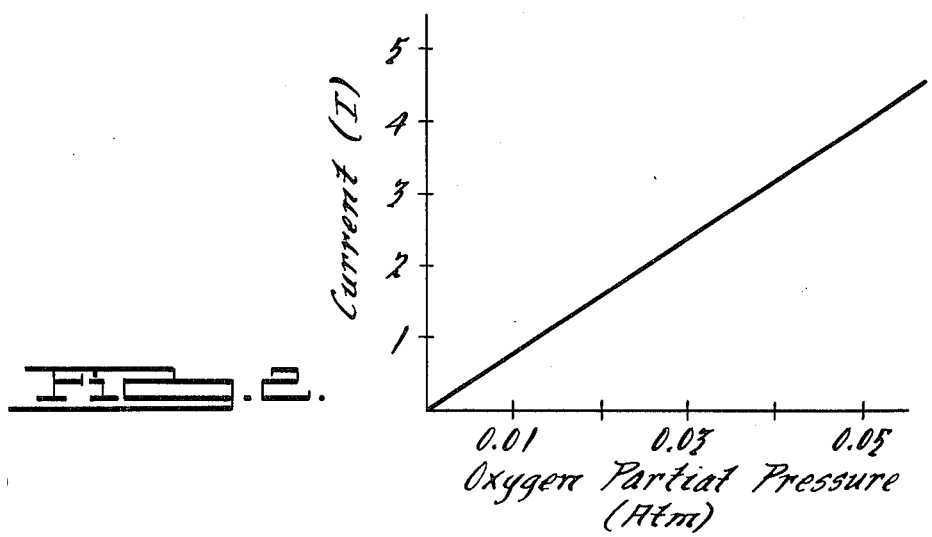
FIG. 2 is a graphical representation of current versus oxygen partial pressure of the device of FIG. 1.

If the device is operated in a manner such that the sensing cell voltage is always the same, then the current required to accomplish this becomes proportional to the ambient oxygen partial pressure $P_x$ as shown in FIG. 2 and is then a measure of the oxygen partial pressure. This type of operation may be effected using electronic circuitry 22. Suitable oxygen and pumping circuitry is described in any of U.S. Pat. Nos. 4,272,329, 4,272,330 or 4,272,331. The disclosures of those patents are incorporated herein by reference.

Oxygen measuring device 10 operates analogously to the prior art disclosed by U.S. Pat. Nos. 4,272,329, 4,272,330 or 4,272,331. However, the volume and aperture defined by the sensing and pumping cells disclosed in the above-referenced prior art are replaced in the present invention with the porosity of electrolyte layer 12. In other words, the porous electrolyte layer 12 serves the dual purpose of providing a solid electrolyte for the pumping cell and an enclosed volume with an aperture for establishing an oxygen gas reference partial pressure.

The two electrolyte layers 12 and 18 are made from the same or different materials chosen from known oxygen conducting solid electrolytes such ZrO$_2$ stabilized with Y$_2$O$_3$ or CeO$_2$. The substrate electrolyte layer 12 is fabricated, for example, as a thin porous platelet by conventional ceramic techniques. The choice of porosity and thickness of this platelet will define the time response of the device and the magnitude of the pumping current. Electrodes 14, 16 and 18 can be made of platinum or other materials which are catalytic with respect to reactions between the chemical species in the ambient of interest and with respect to the reactions of equations (1) and (2). Examples of such materials are Rh and Pd. The electrodes can be deposited as films by such methods as sputtering, thermal evaporation, chemical vapor deposition, electron beam deposition etc. The electrode film thicknesses are generally in the range 0.3 to 1.0 micrometer. The dense solid electrolyte layer 18 is deposited over electrode 16 by one of many available techniques such as sputtering, chemical vapor deposition, printing from ink, etc. The thickness of this layer typically has values in the range 1-10 micrometers, but more could be used depending upon described sensor operating characteristics. Finally, electrode 20 is deposited on electrolyte layer 18. Three electrodes are a further simplification over four electrodes used in some prior art. If desired, thin, porous, protective layers of an inert material (e.g. spinel, alumina) may be deposited on the exposed electrodes 14 and 20 for protection from abrasion.

Any number of techniques for heating sensor device 10 can be used. For example, a ceramic tube wound with a heater wire (e.g. platinum) in which the sensor is mounted can be used. Alternatively, a planar type of heater fabricated directly onto the substrate and using a conducting film as a heating element can be used.

In device 10, the function of the two electrolyte layers 12 and 18 can be interchanged so that, the electrochemical cell including electrode 16, electrolyte layer 18 and electrode 20 is operated as the pumping cell by passing the current I through this cell, whereas the cell including electrode 16, electrolyte layer 12 and electrode 14 functions as the sensing cell. Such an interchange can be accomplished by changing the connections to electronic circuitry 22.

Figure 3:
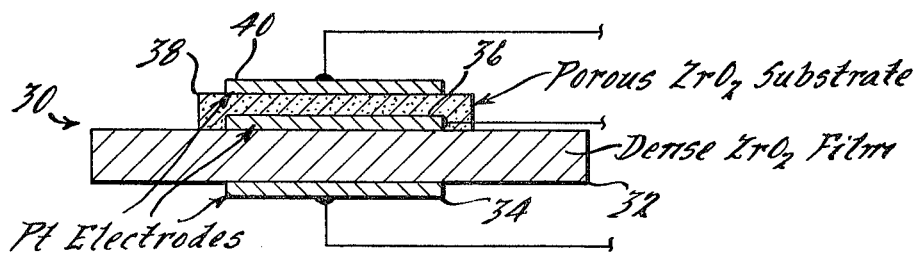
FIG. 3 is a cross section view of a second embodiment of this invention wherein a relatively dense electrolyte material layer is used as the substrate of an oxygen pumping device.

Referring to FIG. 3, an alternate embodiment of the present invention includes a sensor 30 wherein the substrate is a dense and essentially gas-impervious solid electrolyte layer 32. An electrode 34 is positioned on one side of layer 32 and an electrode 36 is positioned on the other side of layer 32. A porous, gas permeable, solid electrolyte layer 38 is formed on electrode 36 and extends over electrode 36 so as to contact layer 32. An electrode 40 is formed on a side of layer 38 opposite from electrode 36. Electrodes 34, 36 and 49 have leads attached thereto for connection to an appropriate electrical circuit, such as circuitry 22 of FIG. 1, for activating the sensor device.

When fabricating sensor device 30, a dense and gas impervious platelet made from yttria stabilized zirconia or other oxygen-conducting solid electrolyte is used as a substrate into which the two platinum (or other appropriate material) electrodes, one on each side, are deposited by one of the methods mentioned in the discussion of the device of FIG. 1. Next, a porous yttria stabilized zirconia or other oxygen-conducting solid electrolyte layer 38 is deposited by a technique such as screen printing, flame spray, chemical vapor deposition etc., followed by another platinum electrode 40. The electrochemical cell comprising the dense electrolyte substrate 32 is used as the oxygen pump whereas the cell comprising the porous electrolyte layer 38 is used as the oxygen-sensing cell. Alternately, the function of the two cells may be reversed.

Figure 4:
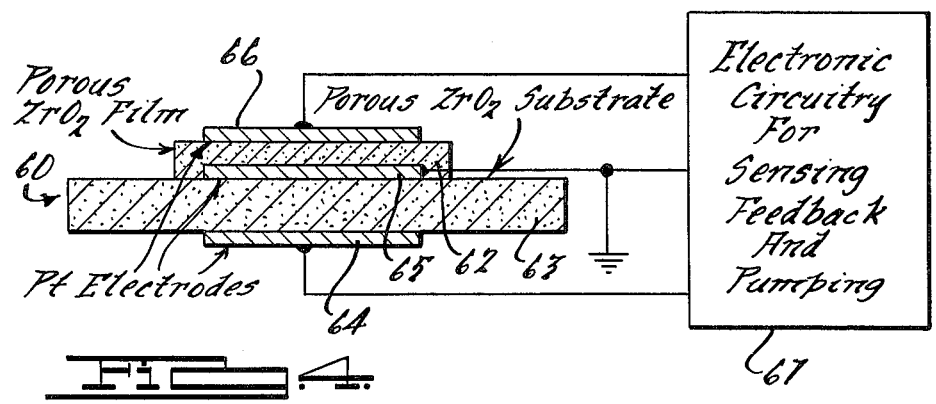
FIG. 4 is a cross section view of an oxygen pumping device in accordance with a third embodiment of this invention wherein two porous layers of electrolyte material are used in the oxygen pumping device.

FIG. 4 is another embodiment of the present invention. A sensor device 60 differs from the sensor devices of FIGS. 1 and 3 in that both solid electrolyte layers 62 and 68 are gas permeable, with the same or different porosity. The use of two porous electrolyte layers facilitates the optimization of the device with respect to response time and pumping current requirement. An electrode 64 is formed on layer 63. An electrode 65 is formed between layers 62 and 63, opposing electrode 64. An electrode 66 is formed on layer 62 opposing electrode 65. As before, sensor device 60 is connected to appropriate electronic circuitry 67.

Figure 5:
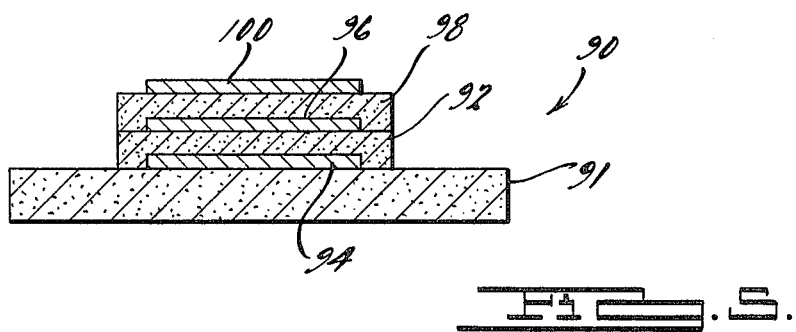
FIG. 5 is a cross section view of an oxygen pumping device in accordance with a fourth embodiment of this invention wherein two electrolyte material layers are formed on a support layer.

Another embodiment of this invention is device 90 of FIG. 5. Device 90 is made by depositing the two solid electrolyte layers 92 and 98 and three electrodes 94, 96, and 100, such as the electrodes of any of the devices in FIGS. 1, 3 and 4, on a relatively thick, mechanically strong porous substrate 91, preferably from the same material as one or both electrolyte layers 92, 98. This type of device is especially useful when both active solid electrolyte layers 92 and 98 are required to be very thin (e.g. for providing low impedance sensing and pumping cells) and thus neither one is mechanically strong to serve as the substrate for the device. One of layers 92 and 98 may be porous or, alternatively, both layers 92 and 98 may be porous.

Various modifications and variations will no doubt occur to those skilled in the various arts to which this invention pertains. For example, the shape of the electrodes and the relative sizes of the solid electrolyte layers may be varied from that described herein. As a further example, the porosity of one or both electrolyte layers may not be uniform but graded (e.g. along the layer thickness). These and all other variations which basically rely on the teachings through which this disclosure has advanced the art are properly considered within the scope of this invention.

We claim:

1. An oxygen pumping device responsive to the oxygen partial pressure in a gas comprising:
   a first oxygen ion conductive solid electrolyte material layer of a first porosity;
   a second oxygen ion conductive solid electrolyte material layer of a second porosity in contact with said first electrolyte material layer, at least one of said first and second porosities having a permeability to gases;
   a first electrode between, and in contact with, said first electrolyte material layer and said second electrolyte material layer,
   a second electrode on said first electrolyte material layer;
   a third electrode on said second electrolyte material layer;
   said first and second electrolyte material layers being a zirconium dioxide material, said first electrolyte material layer having greater porosity than said second electrolyte material layer;
   said first electrolyte material layer being generally planar and having said first and second electrodes positioned on opposing sides,
   said second electrolyte material being generally planar and extending over said first electrode and said first electrolyte material layer so that said first electrode is substantially encapsulated by said first and second electrolyte material layers;

said third electrode being positioned on the opposing side of said second electrolyte material from said first electrode;

a support layer for mechanically supporting said first and second oxygen ion conductive solid electrolyte material layers, said support layer having a permeability to gases;

each of said first and second oxygen conductive solid electrolyte material layers being substantially thinner than said support layer; and said second electrode being formed between said first electrolyte material layer and said support layer.

* * * * *